United States Patent [19]

Klemm

[11] Plant 5,205

[45] Mar. 13, 1984

[54] CARNATION NAMED KLEMORAC

[76] Inventor: Siegfried Klemm, Hanfacker 9, 7000 Stuttgart 50, Fed. Rep. of Germany

[21] Appl. No.: 401,563

[22] Filed: Jul. 26, 1982

[51] Int. Cl.[3] ..... A01H 5/00
[52] U.S. Cl. ..... Plt./70
[58] Field of Search ..... Plt./70

*Primary Examiner*—James R. Feyrer
*Attorney, Agent, or Firm*—Chas. W. Rummler

[57] ABSTRACT

A new spray carnation cultivar particularly distinguished by its continuous profuse production of bright orange flowers of medium size borne singly on strong, erect pedicels which in turn are carried on a strong upright peduncle. This plant has a vigorous and strong and upright growth habit quite similar to that of the unpatented variety Ministar of which this plant is a sport.

1 Drawing Figure

BACKGROUND OF THE NEW PLANT

This new carnation originated as a sport of the variety Ministar (unpatented) and was discovered by me on July 7, 1979 among greenhouse plants of the parent variety being grown at Stuttgart, West Germany for breeding and commercial purposes. The bright and strong coloration of this sport immediately caused me to take the necessary steps to propagate this sport for testing purposes which I did by means of cuttings taken and rooted in my greenhouse at Stuttgart. This manner of propagation of this plant has been carried on at Stuttgart through several successive generations which have shown its novel characteristics to hold true from generation to generation and to appear to be firmly fixed, thereby providing an unusal and attractive carnation cultivar of considerable commercial merit.

DESCRIPTION OF THE DRAWING

My new carnation cultivar is illustrated by the accompanying full color photographic drawing which shows a display of flowers and buds in various stages of blooming, the flower coloration being shown as nearly true as it is reasonably possible to obtain by means of conventional photographic procedures. The density of the coloring at the central portions of the fully opened blooms results from the compactness of the flower petals which are actually of the same color from end to end.

DESCRIPTION OF THE NEW PLANT

The following is a detailed description of my new carnation cultivar based upon observations of plants grown in greenhouses with conventional greenhouse practices, the color designations being according to Robert Wilson's H.C.C. Colour Chart published by the British Color Council in collaboration with The Royal Horticultural Society of London, England.

THE PLANT

Origin: Sport.
Parentage: The variety Ministar (unpatented).
Classification:
*Botanic.*—*Dyanthus caryophyllus.*
*Commercial.*—Greenhouse spray carnation.
Form: Bush.
Height: From about 90 to about 120 cm.

Growth habit: Vigorous and upright with very good strength.
Branching: Normal.
Foliage: Quantity — Moderate.
*Leaf size.*—Moderate.
*Leaf shape.*—Oblong.
*Texture.*—Smooth.
*Color.*—Upper side — Blue-Green. Under side — Blue-Green.

THE BUD

Size: Medium, about 15 mm. in diameter and about 42 mm. long.
Form: Cylindrical.
Opening rate: Moderate.
Color:
*When sepals first divide.*—Yellow-Green.
*When petals begin to unfurl.*—Approaching H.C.C. 610/1 in the portion projecting beyond the sepals.
Sepals:
*Condition.*—Upstanding.
*Color.*—Inside — Grey-Green. Outside — Yellow-Green.
Calyx:
*Size.*—Moderate, about 15 mm. broad and about 17 mm. long.
*Shape.*—Cylindrical.
*Splitting.*—The calyx of this bloom does not split.
*Aspect.*—Smooth.
Pedicels: Rigid and generally upright.
*Color.*—Grey-Green.
Peduncle: Rigid and erect.
*Color.*—Grey-Green.

THE FLOWER

Blooming habit: Continuous and profuse.
Size of bloom: Medium.
*Diameter.*—About 60 to 65 mm.
*Depth.*—About 30 to 35 mm.
Borne: Singly.
Shape: High center when bloom first opens and this form does not change.
Petalage: Moderate, the number of petals being about 38.
*Arrangement.*—Generally imbricated.
*Shape.*—Fan shaped with toothed margins.

*Color.*—Outer and inside petals — H.C.C. 610/1 to 610/2. Reverse side — H.C.C. 610/1.
*Texture.*—Soft.
*Aspect.*—Shiny.
Peduncle: Sturdy and upright.
*Length.*—About 45 cm.
*Color.*—Grey-Green.
Persistence: The flowers hang on and dry.
Fragrance: None.
Lasting quality:
*On the plant.*—About 16 days.
*As a cut flower.*—About 12 days.

REPRODUCTIVE ORGANS

Stamens: Anthers and pollen are rarely present.
Pistils: Few — not more than 3.
*Length.*—About 40 mm.
*Stigmas.*—Color — Cream Yellow.
Fruit: Fertile.
*Shape.*—Cylindrical.
*Color.*—Green/Brown at maturity.

This carnation cultivar is particularly distinguished by the bright orange coloring of its flowers which have deeply serrated or toothed margins. The petals of this variety have no stripes and the color of the petals is even from the innermost to the outer petals, this being particularly so in very hot weather conditions and high light intensity. In wintertime and under low light intensity, the outer petal color may be somewhat deeper and more intensive whereas the inner petals appear more pale. This cultivar has a closed calyx which does not split and, as a whole, the plant has an excellent capacity for continuous and profuse production of very attractive blooms.

I claim:

1. A new and distinctive carnation cultivar, substantially as herein shown and described, characterized by its high productivity of bright orange colored flowers borne singly on rigid, erect pedicels carried in spray arrangement by a sturdy upright peduncle.

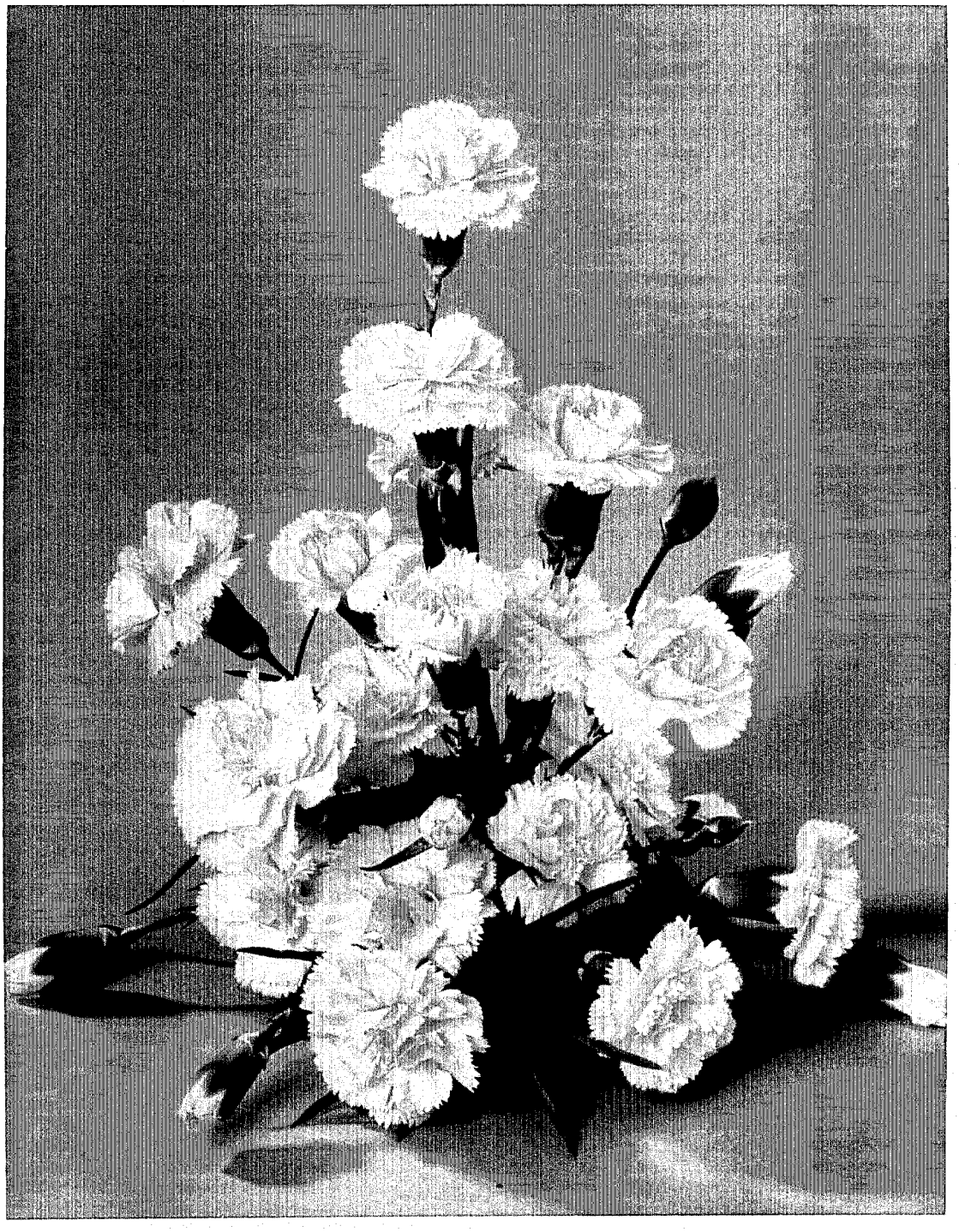

* * * * *